United States Patent [19]

Sovak et al.

[11] Patent Number: 4,863,714
[45] Date of Patent: Sep. 5, 1989

[54] STERILIZATION OF COMPOSITIONS OF LIMITED STABILITY

[75] Inventors: Milos Sovak, Rancho Santa Fe; Stephen J. Foster, San Diego, both of Calif.

[73] Assignee: Cook Imaging Corporation, Bloomington, Ind.

[21] Appl. No.: 11,016

[22] Filed: Feb. 5, 1987

[51] Int. Cl.[4] .............................................. A61K 49/04
[52] U.S. Cl. ........................................... 424/5; 424/4
[58] Field of Search .............................................. 424/5

[56] References Cited

U.S. PATENT DOCUMENTS 4,224,440  9/1980  Smith ........................................ 425/5
4,278,654  7/1981  Rakli et al. ............................... 425/5

Primary Examiner—Frederick E. Waddell
Attorney, Agent, or Firm—Bertram I. Rowland

[57] ABSTRACT

Methods and compositions are provided for producing sterile drug formulations, where drugs are thermolabile and pH sensitive. The method provides formulating the drug with a physiologically acceptable inorganic or organic acidic buffer for buffering at a pH in excess of 6, reducing the pH below about 5 by adding carbon dioxide, and heat sterilizing the formulation in a gas permeable sealed container. The resulting formulation is substantially free of degraded drug and at the desired physiologically acceptable pH. Also, formulations are provided which do not cause clotting during administration.

11 Claims, No Drawings

STERILIZATION OF COMPOSITIONS OF LIMITED STABILITY

TECHNICAL FIELD

Sterilization of drug compositions employing novel protocols and buffer compositions.

BACKGROUND OF THE INVENTION

The preparation of drugs requires that the drugs be sterile. There are a variety of techniques employed for sterilization, including heat, chemicals, such as ethylene oxide, radiation, and the like. One of the most common techniques is the use of heat, particularly steam heat, referred to as autoclaving. In many cases, the drugs are sterilized as liquid formulations. In order for the formulation to be acceptable, it must fulfill a variety of functions.

One of the criteria for many drugs is that the formulation be at an acceptable physiological pH. For some types of drugs, the osmolality of the solution may be significant. In other situations, there may be concern with the particular inorganic cations present, their concentration, and the like. The cations may have pharmacologic effects, for example affecting the stability of the drug, or its physiological acceptability. Thus, in preparing a drug formulation, a number of factors must be considered, not only as to the physiological effect of the components of the drug formulation, but the interaction of the various components, one upon the other, as well as the effect of heat on such interaction and the individual stability of the components.

For non-ionic contract media there are a number of problems associated with intravascular administration by needle or catheter. The hydrophobicity of the contrast media in conjunction with the amino based buffers employed result in clotting. Furthermore, the absence of sodium ions in the medium results in depression of heart function during coronary angiography.

DESCRIPTION OF THE RELEVANT LITERATURE

Radiocontrast Agents, in Handbook of Experimental Pharmacology, ed. M. Sovak, Vol. 73, Springer-Verlag, New York, 1984, provides a broad discussion of contrast media and their properties. U.S. Pat. No. 4,278,654 discusses the use of hydroxyamine buffers in sterilizing radiographic non-ionic contrast media.

SUMMARY OF THE INVENTION

Novel methods and compositions are provided for the sterilization of thermolabile drugs at physiological pH. The method involves employing a weak acid buffer which provides a physiological pH, reducing the pH with carbonate, and autoclaving the resulting formulation in a container under sterile conditions, whereby carbon dioxide may be vented. The resulting drug formulation is sterile and has the desired physiologic pH. The method finds particular application with iodoaryl thermolabile compounds.

DESCRIPTION OF THE SPECIFIC EMBODIMENTS

Methods and compositions are provided involving sterilized drug formulations, where the drug is thermolabile or temperature sensitive at physiologic pH at temperatures necessary for sterilization. The method involves buffering the drug with a weak organic or inorganic acid, particularly an organic carboxylic acid, to a pH which is physiologically acceptable, reducing the pH by introducing carbon dixoxide, particularly at a reduced temperature, and autoclaving at a temperature in excess of 100° C. for sufficient time to sterilize the formulation and expelling the carbon dioxide under sterile conditions. Under these conditions, upon expelling the carbon dioxide, the pH is returned to the physiologic level, while substantially reduced amounts of degradation or modification of the drug occurs.

The subject method can be used with any thermolabile drug, where the thermolability is evidenced at a pH in excess of 5.5, generally in the range of 6 to 8, but is substantially reduced at a pH below 5.5. Thus, the method relies on the transient presence of carbon dioxide in the form of carbonic acid during the sterilization to substantially reduce the degradation of the drug, while allowing for a return of the formulation to physiologic pH after the sterilization. Of particular interest are formulations containing polyiodoaryl compounds, more particularly, radiographic iodo-containing contrast media, such as non-ionic contrast media particularly non-ionic contrast media having N-hydroxyalkyl substituents. For a description of contrast media, see U.S. Pat. Nos. 3,702,866; 4,001,323; 4,021,481, 4,250,113 and 4,341,756.

Contrast media are formulated as aqueous solutions with a pH in the range of about 6–7.5, more usually 6.5–7, desirably 6.7–6.8.

The concentration of the drug in the media may be varied widely. For contrast media, a concentration will generally be about 150–450 mg I/ml. The buffers will be free of amino nitrogen and include carboxylates, phosphates or other physiologically acceptable buffers which provide buffering at the desired pH and allow for pH reduction with carbon dioxide. The organic carboxylic acid buffer may be any convenient water soluble organic carboxylic acid which provides the desired physiological pH. Of particular interest are hydroxycarboxylic acids which are stable under the sterilization conditions, where the carboxylic acid may be mono- or poly-carboxylic acids, particularly of up to about 4, more usually up to about 3 carboxylic acid groups. Illustrative carboxylate buffers include citrate, glycerate, gluconate, glucuronate, saccharate, glucosaccharate, etc. The carboxylate buffers may be substituted or unsubstituted, desirably being substituted with oxy groups, generally having from about 0–5, more usually from about 1–4 oxy groups, particularly hydroxy. In combination with the carboxylate buffer, carbonate, e.g. sodium carbonate, may be added to adjust the pH. The carbonate will generally be in the range of about 0–5 mM, usually 0 to 3 mM.

The concentration of the buffer will be selected so as to be physiologically acceptable and provide the desired stability of the drug. Conveniently, depending upon the buffer, the concentration may range as high as 50 mM, more usually not greater than about 30 mM, usually ranging from about 0.5–25 mM, more usually from about 2–25 mM, particularly 2–5 mM. With non-ionic contrast media, employing citrate as buffer, a particularly desirable concentration is about 3 mM.

The buffer will be desirably present as the sodium salt, although other physiologically acceptable salts may be present, e.g., potassium, so that mixtures may be employed. Preferably, the counterion will be sodium.

Usually, the sodium ion concentration will be somewhere in the range of about 2–20 mN.

The presence of the sodium counterion in non-ionic contrast media is particularly important because of pharmacological benefit. Without sodium, contrast media depress the heart function at the time of coronary angiography. By contrast, amine-based buffers do not provide the necessary sodium and the addition of sodium to the formulation would undesirably increase the osmolality of the formulation resulting in increased vascular pain during angiography.

In addition to the buffer, a physiologically acceptable metal chelating agent may be present, such as ethylenediaminotetraacetic acid (EDTA). EDTA is conveniently employed, generally at a concentration of about 0.5–1.5 mM.

Other additives may also be present for a variety of purposes, depending upon the nature of the drug, the formulation, the manner of administration, or other considerations.

The osmolality of the contrast medium will generally be in the range of about 100–1000 mOs/kg, usually about 150–1000 mOs/kg.

The amount of carbon dioxide which is added to the medium will generally reduce the pH to below about 5.5, preferably below about 5, and usually not less than about 4, mainly ranging from about 4–5, preferably from about 4.3–4.9. The temperature of the solution may be reduced or the pressure raised to dissolve the desired amount of carbon dioxide. Conveniently, the temperature can be reduced, either internally by employing dry ice as the source of $CO_2$ or externally by cooling with an appropriate cooling medium, e.g. ice, ice-saline, etc. Usually, the temperature will be dropped to below 10° C., and can be reduced to just above the freezing point of the medium.

For sterilization, the formulation may be introduced into a container, which is gas permeable, conveniently employing a gas permeable membrane, stopper or the like, depending upon the nature of the container. The container will be capable of withstanding the pressure and temperature of the autoclaving or other heat sterilization. The container may be a permeable plastic bag, plastic or glass vial used in conjunction with stoppers made of teflon, natural or semi-synthetic rubber, silicone rubber, or other conventional gas permeable rubber or stopper. Alternatively, unstoppered containers may be used and the $CO_2$ expelled under sterile conditions, e.g., a sterile room. Syringe needles through a gas-impermeable stopper may be employed to expel the $CO_2$. Other techniques may also be employed.

The autoclaving will normally be carried out under standard conditions as defined by the U.S. Pharmacopeia, i.e., 121° C. for 20 min. During this time, a significant proportion of the carbon dioxide is vented from the formulation and further equilibration is permitted as required to obtain the final pH. Depending upon whether ambient pressures or reduced pressures are employed, equilibration may take as long as twelve days. The equilibration may be greatly speeded up by placing the containers in a vacuum while still at an elevated temperature shortly after the autoclaving or other heat sterilization. At the end of the equilibration, the pH of the product will generally be in the range of about 5.5–8, more usually in the range of about 6–7.5, preferably in the range of about 6.5–7.5.

Of particular interest are contrast media which are polyiodoaryl compounds, particularly benzene derivatives, where the positions which are not iodinated are substituted with amino or carboxy groups. The carboxy groups may be the carboxylic acid, ester, amide, particularly N-alkyl or N-hydroxyalkyl amides and amines, particularly N-hydroxyalkyl acetylamines. Illustrative compounds include 3-N($\beta$-hydroxyethyl)acetamido-5-acetamido-2,4,6-triiodobenzoic acid; 3-(N-hydroxyethylcarbamyl)-5-acetylamino-triiodobenzoic acid; Iohexol; Metrizamide; Iopamidol; 5-(N-2,3-dihydroxypropylacetamido)-N-(2-hydroxyethyl), N'-(2,3-dihydroxypropyl)-2,4,6-triiodoisophthaldiamide (Ioxitol); MP-328 (Mallinckrodt); and 5-N-(2,3-dihydroxypropylacetamido)-2,4,6-triiodo-(N-methyl)-N'-(1,3,4-trihydroxyerythrobut-2-yl)isophthaldiamide.

Formulations of particular interest are the following:

| Formulations | Range | |
|---|---|---|
| | Broad | Narrow |
| Na citrate | 1–5 mM | 1–4 mM |
| EDTA, 2Na | 0.5–1.5 mM | 1–1.5 mM |
| Non-ionic contrast medium | 150–450 mg I/ml | 200–400 mg I/ml |
| Deionized $H_2O$ | q.i.d | q.i.d |

The non-ionic contrast media formulation provides a large number of advantages. The osmolality of the compositions minimize the pain associated with intravascular administration of the compositions. The sodium citrate buffer inhibits clotting during intravascular administration. The presence of the sodium avoids heart function depression. Thus, the subject method of sterilization, not only protects labile compounds from thermal degradation, but in the the use of non-ionic contrast media provides a formulation which has many advantages in administration and physiological properties.

EXPERIMENTAL

The following examples are offered by way of illustration and not by way of limitation.

A number of solutions were prepared having different formulations, where the solutions were adjusted with carbon dioxide prior to autoclaving, to bring the pH of the solution to less than 5 or no carbon dioxide was introduced. The amount of Ioxitol (5-(N-2,3-dihydroxypropylacetamido)-N-(2-hydroxyethyl), N'-(2,3-dihydroxypropyl)-2,4,6-triiodoisophthaldiamide) was 300 mg I/ml. The remaining components and the results are listed in the following table.

TABLE 2

| A. pH of solution adjusted to less than 5 with carbon dioxide prior to autoclaving. | | | |
|---|---|---|---|
| Buffer Solution | pH | | Iodide |
| Na citrate (mM)[1] | before[2] | after[3] | release μg/ml |
| 1 | 6.8 | 6.6 | 8 |
| | 6.8 | 6.5 | 9 |
| | 7.1 | 6.9 | 2 |
| | 7.1 | 6.9 | 1.5 |
| 2 | 6.8 | 6.4 | 9 |
| | 6.8 | 6.4 | 9 |
| | 7.1 | 6.9 | 4 |
| | 7.1 | 6.9 | 5 |
| 3 | 7.1 | 6.7 | 8 |
| 4 | 6.8 | 6.2 | 11 |
| | 7.1 | 7.0 | 9 |
| B. pH of solution not adjusted with $CO_2$ | | | |
| 2[4] | 6.3 | 5.9 | 94 |
| | 6.5 | 6.0 | 122 |
| | 6.8 | 6.3 | 179 |

TABLE 2-continued

| | | | |
|---|---|---|---|
| | 7.1 | 6.2 | 165 |
| 2[5] | 6.0 | 5.8 | 53 |
| | 6.3 | 5.9 | 91 |
| | 6.5 | 6.0 | 135 |
| | 6.8 | 6.0 | 112 |

[1]Solution contains 1.5 mM EDTA, 2 Na.
[2]Adjusted with $Na_2CO_3$; before autoclaving and addition of $CO_2$.
[3]After autoclaving and $CO_2$ equilibration.
[4]2.0 mM citrate, 1.5 mM EDTA to given pH with $Na_2CO_3$.
[5]2.0 mM citrate, 1.5 mM EDTA, 1.5 mM $Na_2CO_3$. The pH was adjusted upwards or downwards with NaOH or HCl, respectively.

It is evident from the above results, that the subject invention provides the ability to sterilize thermolabile pH-sensitive materials at elevated temperatures and substantially prevent their degradation. The procedure is simple, effective, and can be readily employed with a large variety of drugs without adverse effects and provide for physiologically acceptable products.

Although the foregoing invention has been described in some detail by way of illustration and example for purposes of clarity of understanding, it will be obvious that certain changes and modifications may be practiced within the scope of the appended claims.

What is claimed is:

1. A method for heat sterilizing a thermolabile pH sensitive polyiodoaryl composition in an aqueous formulation, said method comprising:
   preparing said formulation comprising said composition, an aqueous buffered medium of a physiologically acceptable organic carboxylic acid buffer other than an amine nitrogen buffer at a pH of greater than about 5.5 and sufficient $CO_2$ to reduce the pH below about 5.5; and
   heating said formulation under sterilizing conditions to sterilize said formulation; and expelling $CO_2$ from said formulation;
   whereby said formulation equilibrates to a pH greater than about 5.5.

2. A method according to claim 1, wherein said buffer provides a pH in the range of 6 to 7.5 and said $CO_2$ reduces the pH to the range of 4 to 5.

3. A method according to claim 1, wherein said buffer is an organic carboxylate buffer.

4. A method according to claim 3, wherein said buffer is citrate.

5. A method according to claim 1, wherein said buffer is an organic carboxylate buffer at a concentration of up to about 50 mM.

6. A method according to claim 1, wherein said sterilization is at a temperature of about 121° C. for about 20 minutes.

7. A method for heat sterilizing a radiographic non-ionic contrast media composition in an aqueous formulation, said method comprising;
   preparing said formulation comprising said composition, an aqueous buffered medium of a physiologically acceptable buffer other than an amine nitrogen buffer at a pH in the range of about 6 to 7.5 and sufficient $CO_2$ to reduce the pH below about 5; and
   heating said formulation in a sealed gas permeable container under sterilizing conditions to sterilize said formulation in said container;
   whereby said $CO_2$ is expelled and said formulation equilibrates to a pH in the range of about 6 to 7.5.

8. A method according to claim 7, wherein said buffer is an organic carboxylate buffer.

9. A method according to claim 8, wherein said buffer is citrate.

10. A method according to claim 7, wherein said buffer is an organic carboxylate buffer at a concentration of up to about 50 mM.

11. A method according to claim 7, wherein said sterilization is at a temperature of about 121° C. for about 20 minutes.

* * * * *